US00PP10051P

United States Patent [19]

Glicenstein

[11] Patent Number: Plant 10,051

[45] Date of Patent: Oct. 7, 1997

[54] ASTER PLANT NAMED 'CELESTE'

[75] Inventor: Leon Glicenstein, Salinas, Calif.

[73] Assignee: Yoder Brothers, Inc., Barberton, Ohio

[21] Appl. No.: 621,865

[22] Filed: Mar. 15, 1996

[51] Int. Cl.[6] ..... A01H 5/00

[52] U.S. Cl. ..... Plt./68.1

[58] Field of Search ..... Plt./68.1

*Primary Examiner*—Howard J. Locker

*Attorney, Agent, or Firm*—Foley & Lardner

[57] ABSTRACT

An Aster plant named Celeste particularly characterized by its cupped capitulum form; daisy capitulum type; violet-blue ray floret color; diameter across face of capitulum of 24 to 27 mm when fully opened; strong, well branched flower stems; many capitula per inflorescence on short peduncles; flowers hold color well as they age; and compact, rounded plant habit.

1 Drawing Sheet

The present invention comprises a new and distinct cultivar of Aster plant, botanically known *Aster pringlei×novi-belgii*, and referred to by the cultivar name Celeste.

Celeste is a product of an open-pollinated breeding program, which had the objective of creating new perennial Aster cultivars for pots, garden and landscape use capable of year-round production, as well as having well branched flower stems, a good plant habit, good flower size, a high-quality blue-violet color and good flower keeping quality. Such combinations were not present in previously available commercial cultivars.

Celeste originated, a stated above, from seed produced on selected parents in an open-pollinated field situation in Salinas, Calif. in October 1991. After harvest the seed was bulked, so that the female and male parents of Celeste are unknown. The seed was sown in Alva, Fla. on Jun. 15, 1992.

Celeste was discovered and selected as one flowering plant within the above progeny under the supervision of Leon Glicenstein in February 1993 in a controlled environment in Alva, Fla., and was identified as Aster seedling No. 0213.

The first act of asexual reproduction of Celeste was accomplished when vegetative cuttings were taken from the initial selection in June 1993 in a controlled environment in Alva, Fla., by a technician working under the supervision of Leon Glicenstein.

Horticultural examination of controlled flowerings of successive plantings has shown that the unique combination of characteristics as herein disclosed for Celeste are firmly fixed and are retained through successive generations of asexual reproduction.

Celeste has not been observed under all possible environmental conditions. The phenotype may vary significantly with variations in environment such as temperature, light intensity and daylength, without, however, any variance in genotype.

The following observations, measurements and comparisons describe plants grown in pots in controlled open areas in Salinas.

The following traits have been repeatedly observed and are determined to be basic characteristics of Celeste, which, in combination, distinguish this Aster as a new and distinct cultivar:

1. Cupped capitulum form.
2. Daisy capitulum type.
3. Violet-blue ray floret color.
4. Diameter across face of capitulum of 24 to 27 mm when fully opened.

5. Strong, well branched flower stems.
6. Many capitula per inflorescence on short peduncles.
7. Flowers hold color well as they age.
8. Compact, rounded plant habit.

The accompanying photographic drawing shows a typical plant of Celeste, with the colors being as nearly true as possible with illustrations of this type.

Of the commercial cultivars known to the inventor, the most similar in comparison to Celeste is the cultivar identified as Blue Butterfly, disclosed in U.S. Plant Pat. No. 7,399. Reference is made to attached Chart A, which compares certain characteristics of Celeste to the same characteristics of Blue Butterfly.

Similar traits are capitulum form and type. Celeste has a darker ray floret color (RHS 90B to 90D) than Blue Butterfly (RHS 92B). Celeste has a more rounded plant habit, a smaller diameter of capitulum, an earlier natural season flower date and a better flower color retention than Blue Butterfly.

In the following description color references are made to The Royal Horticultural Society Colour Chart. The color values were determined on plant material grown outdoors in Leamington, Canada, in September 1995.

Classification:

*Botanical.*—*Aster pringlei×novi-belgii* cv Celeste.

*Commercial.*—Perennial garden or landscape Aster.

Inflorescence

A. Capitulum:

*Form.*—Cupped.

*Type.*—Daisy.

*Diameter across face.*—24 to 27 mm when fully opened.

B. Corolla of ray florets:

*Color (general tonality from a distance of three meters).*—Blue-violet.

*Color (upper surface).*—Between 90B and 90D.

*Color (under surface).*—90D.

*Shape.*—Narrow, oblanceolate to linear, apex obtuse.

*Size.*—9 to 12 mm long, 1 to 2 mm wide.

*Number of ray florets.*—26 to 30.

C. Corolla of disc florets:

*Color (mature).*—Between 155A to 155B and 1D.

*Color (immature ).*—*Between* 1C and 1D.

D. Reproductive organs:

*Androecium.—Present on disc florets only; scant pollen.*

*Gynoecium.*—Present on both ray and disc florets.

Plant

A. General Appearance:

*Height.*—23 to 24 cm when grown in fall under natural daylength with no growth regulators.

*Habit.*—Rounded mound.

B. Foliage:

*Color (upper surface).*—137A.

*Color (under surface).*—146B.

*Shape.*—Oblanceolate and linear, attenuated leaf base and acute leaf tip.

*Size.*—90 to 100 mm long, 12 to 6 mm wide.

*Margin.*—Entire.

*Arrangement.*—Alternate.

CHART A

| CULTIVAR | CELESTE | BLUE BUTTERFLY |
|---|---|---|
| Ray floret color | Blue-violet | Blue-violet |
| Capitulum form and type | Cupped daisy | Cupped daisy |
| Diameter across face of capitulum | 24 to 27 mm | 27 to 30 mm |
| Plant habit | Rounded mound | Upright mound |
| Nat. season flower date | Aug 13 to 19 | Aug 17 to 23 |
| Color retention | Good | Poor |

COMPARISONS MADE OF PLANTS GROWN UNDER NATURAL SEASON OUTDOOR CONDITIONS IN SALINAS, CALIFORNIA

What is claimed is:

1. A new and distinct Aster plant named Celeste, as described and illustrated.

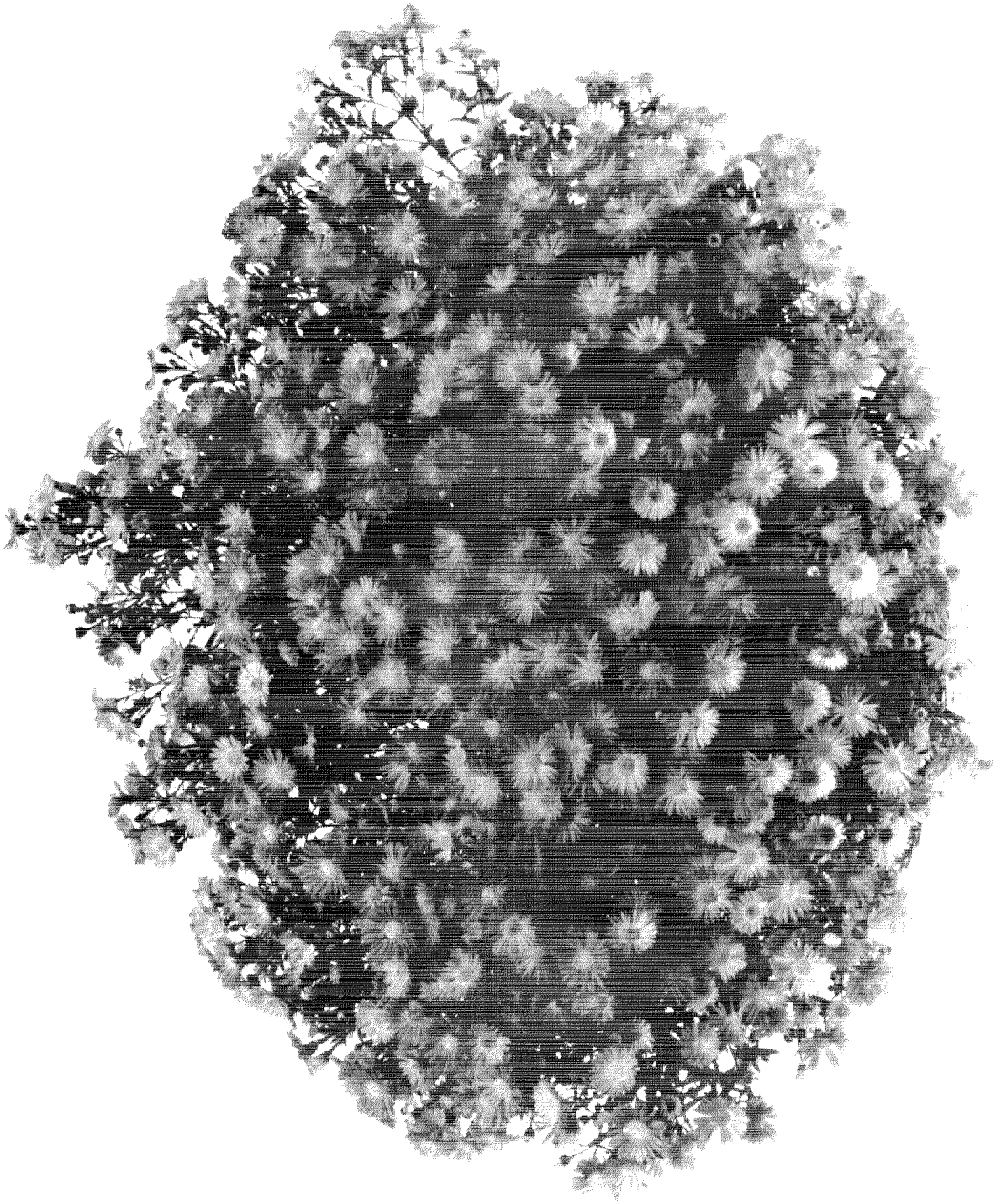

* * * * *